United States Patent
Konishi et al.

(10) Patent No.: US 10,961,658 B2
(45) Date of Patent: *Mar. 30, 2021

(54) METHOD FOR RECOVERING PULP FIBER FROM USED SANITARY PRODUCT AND RECYCLED PULP OBTAINED THEREBY

(71) Applicant: UNICHARM CORPORATION, Ehime (JP)

(72) Inventors: Takayoshi Konishi, Kagawa (JP); Toshio Hiraoka, Kagawa (JP); Noritomo Kameda, Kagawa (JP); Hideaki Ichiura, Kochi (JP); Hiroko Nakaoka, Kochi (JP)

(73) Assignee: UNICHARM CORPORATION, Ehime (JP)

( * ) Notice: Subject to any disclaimer, the term of this patent is extended or adjusted under 35 U.S.C. 154(b) by 30 days.

This patent is subject to a terminal disclaimer.

(21) Appl. No.: 16/431,213

(22) Filed: Jun. 4, 2019

(65) Prior Publication Data

US 2019/0291303 A1    Sep. 26, 2019

Related U.S. Application Data

(60) Continuation of application No. 16/262,849, filed on Jan. 30, 2019, which is a division of application No. 15/512,443, filed as application No. PCT/JP2015/072542 on Aug. 7, 2015, now Pat. No. 10,260,199.

(30) Foreign Application Priority Data

Sep. 22, 2014 (JP) ................................. 2014-193074

(51) Int. Cl.
| | |
|---|---|
| *D21C 5/02* | (2006.01) |
| *A61L 2/18* | (2006.01) |
| *A61L 11/00* | (2006.01) |
| *B09B 3/00* | (2006.01) |
| *B09B 5/00* | (2006.01) |
| *B29B 17/02* | (2006.01) |
| *B29B 17/04* | (2006.01) |
| *C08J 11/10* | (2006.01) |
| *C08J 11/16* | (2006.01) |
| *D21B 1/32* | (2006.01) |
| *B29L 31/48* | (2006.01) |

(52) U.S. Cl.
CPC ............ *D21C 5/022* (2013.01); *A61L 2/18* (2013.01); *A61L 11/00* (2013.01); *B09B 3/00* (2013.01); *B09B 5/00* (2013.01); *B29B 17/02* (2013.01); *B29B 17/04* (2013.01); *C08J 11/10* (2013.01); *C08J 11/16* (2013.01); *D21B 1/32* (2013.01); *D21C 5/02* (2013.01); *B29B 2017/0289* (2013.01); *B29L 2031/4878* (2013.01); *Y02W 30/62* (2015.05); *Y02W 30/64* (2015.05)

(58) Field of Classification Search
USPC .......................................................... 162/4
See application file for complete search history.

(56) References Cited

U.S. PATENT DOCUMENTS

| | | | |
|---|---|---|---|
| 5,336,372 A |  | 8/1994 | Cody et al. |
| 10,260,199 B2 | * | 4/2019 | Konishi ............... A61L 2/18 |
| 2016/0237617 A1 |  | 8/2016 | Yamaguchi et al. |

FOREIGN PATENT DOCUMENTS

| | | |
|---|---|---|
| EP | 1 415 733 A1 | 5/2004 |
| JP | H04317785 | 11/1992 |
| JP | H06009121 | 1/1994 |
| JP | H06184970 | 7/1994 |
| JP | H08013381 | 1/1996 |
| JP | 2000-084533 A | 3/2000 |
| JP | 2001-047023 A | 2/2001 |
| JP | 2003-039023 A | 2/2003 |
| JP | 2009-073198 A | 4/2009 |
| JP | 2009-183893 A | 8/2009 |
| JP | 2012-067406 A | 4/2012 |
| JP | 2014-217835 A | 11/2014 |
| JP | 2015-86483 A | 5/2015 |
| KR | 10-1044439 B1 | 6/2011 |
| WO | WO 94/20668 | 9/1994 |

OTHER PUBLICATIONS

International Search Report from corresponding PCT application No. PCT/JP2015/072542 dated Sep. 8, 2015 (6 pgs).
"Air and Water Ozone Disinfection Concentration Standard," *Quapure*, https://aquapureozone.com/2018/07/06/ozone-disinfection-concentration-standard, 4 pp. (2020).
"Ozone reaction mechanisms," https://www.lenntech.com/library/ozone/reaction/ozone-reaction- mechanisms.htm#ixzz6fTm8YUN3 9 pp. (2020).

* cited by examiner

*Primary Examiner* — Mark Halpern
(74) *Attorney, Agent, or Firm* — Brinks Gilson & Lione; Yuezhong Feng

(57) ABSTRACT

Pulp fiber containing little ash is effectively recovered from a used sanitary product containing the pulp fiber and a polymer absorbent. The method according to the present invention comprises: a step for treating the used sanitary product with an ozone-containing gas and thus decomposing and removing at least a portion of the polymer absorbent in the used sanitary product; and a step for stirring the used sanitary product, that has been treated with the ozone-containing gas, in water or an aqueous solution containing an antiseptic and thus decomposing the used sanitary product into constituents. If required, the method may further comprise a step for separating the pulp fiber from the decomposition product obtained by the decomposition step.

14 Claims, No Drawings

METHOD FOR RECOVERING PULP FIBER FROM USED SANITARY PRODUCT AND RECYCLED PULP OBTAINED THEREBY

RELATED APPLICATION

This application is a continuation of Non-Provisional patent application Ser. No. 16/262,849, filed Jan. 30, 2019, which is divisional application of Non-Provisional application Ser. No. 15/512,443, filed Mar. 17, 2017 which is a 35 U.S.C. § 371 national phase filing of International Patent Application No. PCT/JP2015/072542, filed Aug. 7, 2015. Priority is hereby claimed under 35 U.S.C. § 120 to Non-Provisional patent application Ser. Nos. 16/626,849 and 15/512,443 and under 35 U.S.C. § 119 to Japanese Patent Application No. 2014-193074, filed Sep. 22, 2014, the complete disclosures of each of which are hereby expressly incorporated by reference.

TECHNICAL FIELD

The present invention relates to a method for recovering pulp fiber from used sanitary products, and to recycled pulp obtained by the method. In, particular, the invention relates to a method for recovering pulp fiber from used sanitary products such as used disposable paper diapers that include pulp fiber and a polymer absorbent, and to recycled pulp obtained by the method.

BACKGROUND ART

It has been attempted to recycle used sanitary products such as disposable paper diapers. For recycling of used sanitary products, it is common to disintegrate the used sanitary products in water, separating them into the constituent components of the sanitary products, which are then recovered. However, the polymer absorbents that are included in sanitary products absorb moisture and increase in mass, while also gelling and losing their flow property, causing the throughput capacity of the treatment apparatus to be reduced.

Patent Document 1 therefore discloses using lime for dehydration of polymer absorbents in used paper diapers that have absorbed moisture (claim 2). This reduces the weight of the polymer absorbent, while also restoring the gel state to the original state and recovering its flow property, so that reduction in the throughput capacity of the treatment apparatus can be avoided (paragraph [0020]).

PRIOR ART DOCUMENTS

Patent Documents

Patent Document 1: JP 2009-183893 A

SUMMARY OF THE INVENTION

Problems to be Solved by the Invention

A polymer absorbent that has been dehydrated using lime, as described in Patent Document 1, becomes a solid powder with a particle size of several μm to several hundred μm, and such micro particles are particularly prone to being caught up between pulp fibers and cannot be completely removed by simple physical water rinsing. When it is attempted to reuse pulp fibers recovered in this manner, the residual polymer absorbent not only remains as a contaminant but also forms calcium salts, and therefore the recovered pulp fiber is more likely to have a detected ash content above the reference value for sanitary products.

Means for Solving the Problems

The present invention, which has been devised in light of the aforementioned problems of the prior art, is a method for recovering pulp fiber from a used sanitary product including pulp fiber and a polymer absorbent, comprising the steps of:

treating the used sanitary product with an ozone-containing gas to decompose and remove at least a portion of the polymer absorbent in the used sanitary product, and stirring the used sanitary product that has been treated with the ozone-containing gas, in a disinfectant-containing aqueous solution or in water to decompose the used sanitary product into its constituent elements.

The ozone concentration of the ozone-containing gas is preferably 50 to 200 $g/m^3$.

The treatment time with the ozone-containing gas is preferably 10 to 60 minutes.

Preferably, the used sanitary product is treated with the ozone-containing gas so that at least 90% of the polymer absorbent in the used sanitary product is decomposed and removed.

The disinfectant is preferably sodium hypochlorite, chlorine dioxide, acidic electrolyzed water, ozone water, acidic ozone water or organic acid-containing ozone water.

The method preferably further comprises a step of separating the pulp fiber from the decomposition product obtained by the decomposing step.

The method also preferably comprises a step of separating apart at least a portion of the elements composing the used sanitary product and/or breaking up a portion of the used sanitary product before the step of treating the used sanitary product with an ozone-containing gas to decompose and remove at least a portion of the polymer absorbent in the used sanitary product.

Preferably, the method further comprises a step of drying the pulp fiber, the step of drying the pulp fiber resulting in dried pulp fiber having a moisture content of 5 to 13%.

The pulp fiber is preferably dried at a temperature of 100 to 200° C.

The present invention is also recycled pulp having an ash content of not more than 0.8 percent by weight and a water absorption factor of not less than 12 times, obtained by a method for recovering pulp fiber from a used sanitary product including pulp fiber and a polymer absorbent, the method comprising the steps of:

treating the used sanitary product with an ozone-containing gas to decompose and remove at least a portion of the polymer absorbent in the used sanitary product, and stirring the used sanitary product that has been treated with the ozone-containing gas, in a disinfectant-containing aqueous solution or in water to decompose the used sanitary product into its constituent elements.

The recycled pulp preferably has an ash content of not more than 0.65 percent by weight.

The recycled pulp preferably has a moisture content of 5 to 13%.

Effect of the Invention

The invention decomposes and removes a polymer absorbent in a used sanitary product with ozone-containing gas, and thus allows the pulp fiber to be efficiently recovered while regenerating pulp fiber with a low ash content.

MODE FOR CARRYING OUT THE INVENTION

The invention is a method for recovering pulp fiber from used sanitary products that include pulp fiber and a polymer absorbent.

The sanitary products are not particularly restricted so long as they contain pulp fiber and a polymer absorbent, and examples include disposable paper diapers, urine-absorbing pads, sanitary napkins and panty liners.

There are no particular restrictions on the pulp fiber, and examples include fluffy pulp fiber and chemical pulp filaments.

A polymer absorbent, also known as super-absorbent polymer (SAP), has a three-dimensional network structure with an appropriately crosslinked water-soluble polymer and therefore absorbs a few hundred to a few thousand times its weight of water, but it is essentially water-insoluble and the absorbed water does not emerge even with some degree of pressure application. Examples thereof include starch-based, acrylic acid-based and amino acid-based particulate or fibrous polymers.

The method of the invention comprises:

a step of treating the used sanitary product with an ozone-containing gas to decompose and remove at least a portion of the polymer absorbent in the used sanitary product, and a step of stirring the used sanitary product that has been treated with the ozone-containing gas, in a disinfectant-containing aqueous solution or in water to decompose the used sanitary product into its constituent elements.

If necessary, the method of the invention may further comprise:

a step of separating apart at least a portion of the elements composing the used sanitary product and/or breaking up a portion of the used sanitary product before the step of treating the used sanitary product with an ozone-containing gas to decompose and remove at least a portion of the polymer absorbent in the used sanitary product, a step of separating the pulp fiber from the decomposition product obtained by the decomposing step, a step of rinsing the separated pulp fiber with water, a step of dehydrating the rinsed pulp fiber, and a step of drying the pulp fiber.

The method of the invention comprises a step of treating a used sanitary product with an ozone-containing gas to decompose and remove at least a portion of the polymer absorbent in the used sanitary product (this step will hereunder be referred to simply as "ozone treatment step").

For this step, the polymer absorbent is decomposed, the majority thereof being gasified as $CO_2$ and being discharged together with the ozone-containing gas, with only a very small amount flowing out as liquid.

The "ozone-containing gas" used in this step is a gas that contains ozone. The ozone-containing gas may be prepared using, for example, an ozone generator (such as an ED-OWX-2 ozone gas exposure tester by EcoDesign, Inc. or an OS-25V ozone generator by Mitsubishi Electric Corp.). The gases other than ozone in the ozone-containing gas are not particularly restricted so long as they do not inhibit the decomposing power of the ozone, and possible examples include air, oxygen, nitrogen, argon and carbon dioxide, but since nitrogen reacts with water during production of ozone, forming nitric acid which can adversely affect equipment, it is therefore preferred to use oxygen alone or denitrified air, or dry air.

The ozone concentration of the ozone-containing gas is not particularly restricted so long as it is a concentration allowing decomposition of the polymer absorbent, but it is preferably 50 to 200 $g/m^3$, more preferably 60 to 150 $g/m^3$ and even more preferably 70 to 120 $g/m^3$. If the concentration is too low, it will not be possible to adequately decompose the polymer absorbent, and the polymer absorbent may remain in the recovered pulp fiber. If the concentration is too high, conversely, the oxidizing power will increase, potentially damaging the pulp fiber and possibly causing problems in terms of safety.

The treatment time with the ozone-containing gas is not particularly restricted so long as it is a time allowing the polymer absorbent to be decomposed. The treatment time with the ozone-containing gas may be short if the ozone concentration of the ozone-containing gas is high, while a longer time will be required if the ozone concentration of the ozone-containing gas is low.

The product of the ozone concentration ($g/m^3$) of the ozone-containing gas and the treatment time (min) with the ozone-containing gas (hereunder also referred to as the "CT value") is preferably 500 to 12,000 $m^{-3} \cdot g \cdot min$, more preferably 600 to 10,000 $m^{-3} \cdot g \cdot min$ and even more preferably 1000 to 8000 $m^{-3} \cdot g \cdot min$. If the CT value is too small, it will not be possible to adequately decompose the polymer absorbent, and the polymer absorbent may remain in the recovered pulp fiber. Conversely, an excessively large CT value may result in damage to the pulp fiber, reduced safety and increased manufacturing cost.

The time for treatment with the ozone-containing gas will depend on the ozone concentration of the ozone-containing gas as explained above, but it is preferably 10 to 60 minutes, more preferably 12 to 50 minutes and even more preferably 20 to 40 minutes.

The method of treating the used sanitary product with the ozone-containing gas in the ozone treatment step is not particularly restricted, and for example, the used sanitary product may be placed in a treatment vessel and the ozone-containing gas circulated into the treatment vessel to conduct ozone treatment of the used sanitary product. The temperature in the ozone treatment step is not restricted so long as it allows the polymer absorbent in the used sanitary product to be decomposed, and it is preferably 10 to 50° C., or simply room temperature. The treatment vessel is an apparatus such as a rotary drum-type washing machine, for example, equipped with an ozone-containing gas supply port, a water shower supply port, a gas outlet and a drainage port. When the used sanitary products are used diapers, the used diapers are broken up and loaded, and the solid matter such as feces are softened by water showering and washed out together with drainage water. If desired, a loosener such as a ball mill may also be placed in the drum while the contents are rotating.

In the ozone treatment step, the polymer absorbent is subjected to the oxidative decomposing action of the ozone, whereby the three-dimensional network structure of the polymer absorbent collapses, resulting in low molecularization and liquefaction, and further progressing decomposition results in gasification (to $CO_2$). The hot-melt adhesive used for bonding in the sanitary product also undergoes oxidative degradation by the ozone, weakening the bonding strength between the constituent elements of the sanitary product, and therefore stirring in a disinfectant-containing aqueous solution or in water in the subsequent step can easily decompose the used sanitary products to their constituent elements. For example, the used sanitary product can be disintegrated in a simple manner using a washing machine. The bactericidal action of the ozone in the ozone treatment step also accomplishes primary disinfection of the used sanitary products.

The polymer absorbent in the used sanitary product that has absorbed water increases in mass while also gelling and losing its flow property, such that the performance of the processing apparatus is reduced, and it is therefore necessary to inactivate the water-absorbing function of the polymer absorbent; however, treatment with lime or a polyvalent metal salt such as calcium chloride as in the prior art is based on dehydrating action that utilizes difference in ionic osmotic pressure, and in the case of a polyvalent metal salt, crosslinking (crosslinking with Ca in the case of lime) takes place and thus prevents water reabsorption, so that the particles that contained moisture shrink to nearly their state before water absorption, with some of the shrunken particles getting caught on the pulp fiber and becoming difficult to shed. As a result, the Ca crosslinked product resides in the recovered pulp fiber and the Ca crosslinked product is detected as ash, making it difficult to obtain recycled pulp with a low ash content.

With treatment by the ozone-containing gas of the invention, however, oxidative decomposition takes place by the ozone gas, causing cleavage of the molecular chains and low molecularization, so that the three-dimensional network structure of the polymer absorbent collapses and water retention is lost. Moreover, progressive oxidation of ozone gas causes formation of $CO_2$ gas which is discharged as exhaust gas together with the discharged ozone-containing gas, leaving almost no residual particulate matter. It is thus possible to recover high-purity pulp fiber with few contaminants.

When the polymer absorbent is in a dry state, however, it is decomposed only by the oxidative power of ozone gas, without generation of hydroxy radicals (OH) that have stronger oxidative power than ozone, and the efficiency is very poor. It may even undergo virtually no decomposition, depending on the conditions. In order to generate hydroxy radicals, the polymer absorbent may be imbibed with water in an amount of at least equal to, preferably at least 5 times and more preferably at least 10 times its own weight, and contacted with the ozone gas in its moisture-containing state, which will allow generation of hydroxy radicals and efficient oxidative decomposition of the polymer absorbent.

Because ozone gas has very strong oxidative power, an ozone concentration of higher than 200 $g/m^3$ will cause rapid deterioration of the materials composing the diaper such as the film and nonwoven fabric, rendering them fragile and separated into individual powder during treatment.

Prior to the ozone treatment step, there may be provided a step in which at least a portion of the elements composing the used sanitary product are separated apart and/or a portion of the used sanitary product is broken up. The method of separating apart at least a portion of the elements composing the used sanitary product or the method of breaking up a portion of the used sanitary product is not restricted, and for example, the liquid-impermeable film of the used sanitary product may be peeled off and the used sanitary product cut into approximately 5 cm squares with scissors. By providing this step it is possible to facilitate circulation of the ozone-containing gas in the used sanitary product, and increase contact of the polymer absorbent in the used sanitary product with the ozone, thereby promoting decomposition of the polymer absorbent. For example, when the ozone treatment is carried out in an exposure tank, ozone treatment can be accomplished by simple placement in the exposure tank without breakup of the used sanitary product, but since inconsistency of treatment may result if the interior of the exposure tank is not stirred, and can potentially lower the treatment efficiency, in cases where the exposure tank lacks a stirring mechanism it is preferred to break up the used sanitary product to some extent in the initial stage and contact it with the ozone gas in a distributed manner, in order to reduce inconsistency of treatment. If the exposure tank rotates to cause stirring of the interior, as with a drum-type washing machine, there is no need for the initial breakup.

The next step of the ozone treatment step is a step in which the used sanitary product that has been treated with the ozone-containing gas is stirred in a disinfectant-containing aqueous solution or in water to decompose the used sanitary product into its constituent elements (this will hereunder be referred to as "rinsing/decomposing step").

The water to be used in the rinsing/decomposing step does not necessarily have to include a disinfectant, but an aqueous solution containing a disinfectant may be used. The disinfectant is not particularly restricted and may be sodium hypochlorite, chlorine dioxide, acidic electrolyzed water, ozone water or the like, among which sodium hypochlorite is preferred from the viewpoint of economy and general utility.

When an aqueous solution containing a disinfectant is used, the concentration of the disinfectant in the disinfectant-containing aqueous solution is not particularly restricted so long as a disinfecting effect is exhibited, but is preferably 10 to 300 ppm by mass, more preferably 30 to 280 ppm by mass and even more preferably 50 to 250 ppm by mass. If the concentration is too low, it will not be possible to obtain a sufficient disinfecting effect, and bacteria and the like may reside in the recovered pulp fiber. Conversely, if the concentration is too high, not only will the disinfectant tend to be wasted but the pulp fiber may also be damaged, and problems of safety may arise.

The stirring in the rinsing/decomposing step is not particularly restricted so long as the used sanitary product is rinsed and decomposed into its constituent elements, and it may be carried out using a washing machine, for example. The stirring conditions are also not particularly restricted so long as the used sanitary product is rinsed and decomposed into its constituent elements, and for example, the stirring time is preferably 5 to 60 minutes, more preferably 10 to 50 minutes and even more preferably 20 to 40 minutes.

In the rinsing/decomposing step, the used sanitary product from which the polymer absorbent has been removed is rinsed while the sanitary product is decomposed into its separate constituent elements. In the ozone treatment step, the hot-melt adhesive used for bonding in the sanitary product undergoes oxidative degradation by the ozone, thereby weakening the bonding strength between the constituent elements of the sanitary product, so that the sanitary product can be more easily decomposed into its constituent elements by stirring in the rinsing/decomposing step. When a disinfectant-containing aqueous solution has been used, disinfection is also carried out by the disinfectant.

The next step is a step of separating the pulp fiber from the decomposition product obtained by the rinsing/decomposing step (this step will hereunder be referred to as "pulp fiber separating step").

The method of separating the pulp fiber from the decomposition product obtained in the rinsing/decomposing step is not restricted, and for example, it may be carried out by skimming off the pulp fiber floating on the surface of the liquid containing the decomposition product, obtained from the rinsing/decomposing step.

The next step is a step of rinsing the separated pulp fiber (hereunder referred to as "pulp fiber rinsing step").

The method for rinsing the separated pulp fiber is not particularly restricted, and for example, it may be carried out by placing the separated pulp fiber in a mesh bag and rinsing it with water. Water rinsing can be carried out in a batch system or a semi-batch system, or even in a circulating system. When carried out in a batch system, the water rinsing may be performed using a washing machine, for example.

The rinsing conditions are not particularly restricted so long as they allow adequate removal of substances other than the pulp fiber, and for example, the rinsing time is preferably 3 to 60 minutes, more preferably 5 to 50 minutes and even more preferably 10 to 40 minutes. When carried out in a batch system, the amount of water used is preferably 500 to 5000 parts by mass, more preferably 800 to 4000 parts by mass and even more preferably 1000 to 3000 parts by mass, with respect to 100 parts by mass (absolute dry mass) of the pulp fiber.

The next step is a step of dehydrating the rinsed pulp fiber (hereunder be referred to as "pulp fiber dehydrating step").

The method for dehydrating the rinsed pulp fiber is not particularly restricted, and for example, it may be carried out by dehydrating the rinsed pulp fiber placed in the mesh bag, using a dehydrator.

The dehydrating conditions are not particularly restricted so long as they allow the moisture content to be lowered to the target value, but for example, the dehydrating time is preferably 1 to 10 minutes, more preferably 2 to 8 minutes and even more preferably 3 to 6 minutes.

The pulp fiber rinsing step and the pulp fiber dehydrating step may each be carried out once, or they may be repeated several times in an alternating fashion.

The final step is a step of drying the dehydrated pulp fiber (hereunder referred to as "pulp fiber drying step").

The method for drying the dehydrated pulp fiber is not particularly restricted, and for example, it may be accomplished using a dryer such as a hot air drier.

The drying conditions are not particularly restricted so long as they allow adequate drying of the pulp fiber, and for example, the drying temperature is preferably 100 to 200° C., more preferably 110 to 180° C. and even more preferably 120 to 160° C. The drying time is preferably 10 to 120 minutes, more preferably 20 to 80 minutes and even more preferably 30 to 60 minutes.

The moisture content of the dried pulp fiber is preferably 5 to 13%, more preferably 6 to 12% and even more preferably 7 to 11%. If the moisture content is too low, the hydrogen bonds may become too strong resulting in excessive hardness, while conversely if the moisture content is too high, mold and the like may be generated.

The moisture content of the pulp fiber is measured in the following manner. The measurement is conducted in an atmosphere of 20° C.±1° C.

(1) The mass A (g) of the vessel into which the sample to be measured will be placed (a non-covered vessel) is measured.

(2) Approximately 5 g of the sample to be measured is prepared and placed in the vessel whose mass was measured in (1), and the mass B (g) of the sample-containing vessel is measured.

(3) The sample-containing vessel is placed for 2 hours in an oven set at a temperature of 105° C.±3° C.

(4) The sample-containing vessel is removed from the oven and placed for 30 minutes in a desiccator (desiccant: colored silica gel containing substance).

(5) The sample-containing vessel is removed from the desiccator and the mass C (g) is measured.

(6) The moisture content (%) is calculated by the following formula.

$$\text{Moisture content (\%)}=(B-C)/(C-A)\times 100$$

The method of the invention may further comprise a step of separating and recovering the plastic materials (hereunder referred to as "plastic material separating/recovering step"). The plastic materials referred to here are nonwoven fabric materials, film materials, elastomer materials and the like. The plastic material separating/recovering step may be carried out after the rinsing/decomposing step, simultaneously with the pulp fiber separating step. The plastic material separating/recovering step may comprise a rinsing step, dehydrating step and drying step similar to the pulp fiber rinsing step, the pulp fiber dehydrating step and the pulp fiber drying step described above. The recovered plastic materials may be subjected to RPF treatment, for example, and reutilized as solid fuel.

The following is a typical process flow for recovering pulp fiber from used diapers utilizing the method of the invention.

(1) Weighing step (with optional break-up of the diapers).
(2) Treatment step with ozone-containing gas (Decomposition of SAP, along with primary disinfection, bleaching, deodorizing and contaminant decomposition. In this step, most of the SAP is converted to $CO_2$ and is discharged.)
(3) Rinsing/product decomposing step (May be with a common cleanser or water rinsing since no SAP is included.)
(4) Separating step
(5) Pulp fiber recovery
(6) Dehydrating step
(7) Drying step (secondary disinfection)

The plastic materials are recovered from the decomposition product of the rinsing/product decomposing step (3), dried (secondary disinfection) and subjected to RPF treatment.

In the initial stage, the recovered diapers are subjected to ozone gas treatment, the SAP undergoing oxidative decomposition by the oxidative power of the ozone (swelled particulates→disintegration→gasification), with primary disinfection, and in the subsequent rinsing step, the contaminants that could not be decomposed by the ozone gas are treated by rinsing and with a cleanser if necessary, after which the pulp fiber and other materials (such as plastic materials) are separated and each are heat dried for drying and heat disinfection (secondary). Dissolution and removal of the SAP in the initial stage allows efficient recycling in a simple step, and using ozone gas for decomposition of the SAP allows multibarrier disinfection up to a secondary level, so that a high level of safety can be guaranteed.

By carrying out oxidative decomposition of the polymer absorbent with ozone gas according to invention, the gel state of the polymer absorbent disintegrates to a low molecular form, becoming liquid, and further gasifies (to $CO_2$), so that the polymer absorbent does not remain in the pulp fiber and pulp with an ash content conforming to hygienic material standards can be efficiently recovered.

Since the method of the invention does not use metal salts such as lime for inactivation of the water-absorbing function of the polymer absorbent, no ash content is detected from the inactivated polymer absorbent (Ca crosslinked product). Moreover, since the polymer absorbent is decomposed and removed in the method of the invention, there is no loss of the flow property in the treatment tank by the swelled polymer absorbent, and the performance of the processing apparatus is not reduced. Furthermore, since the method of the invention allows high concentration treatment with an ozone concentration of 50 to 200 g/m$^3$, it is possible to accomplish efficient decomposition and gasification of polymer absorbent materials in a short period of time, and the treatment can be carried out in a safe manner. In addition, the method of the invention provides an effect of not only decomposition of the polymer absorbent by the oxidizing action of ozone, but also sterilization, bleaching, decomposition of contaminants and deodorizing, so that high-quality recycled pulp can be obtained. Moreover, the method of the invention is safe because ozone gas has a very short half-life and does not remain in the recycled pulp after treatment. When treatment of the polymer absorbent progresses so that it is gasified (to $CO_2$), contaminants in the rinse drainage can be reduced and the waste water treatment load can be alleviated.

The invention also provides recycled pulp having an ash content of no greater than 0.8 percent by weight and a water absorption factor of 12× or greater, obtained by a method for recovering pulp fiber from used sanitary products that include pulp fiber and a polymer absorbent. The recycled pulp referred to here is that recovered and treated from pulp of used sanitary products. An absorbent article will exhibit different performance (a different water absorption factor of the pulp), depending on the ash content ratio of the recycled pulp. The recycled pulp obtained by the method of the invention is treated using ozone-containing gas so that the water absorption factor is at or above a constant value.

The ash content is the amount of inorganic substances or nonflammable residue remaining after the organic substances have been ashed. The ash content is measured according to the Sanitary Product Material Standards "2. General test methods", "5. Ash content test method". Specifically, the ash content is measured in the following manner.

A platinum, quartz or magnetic crucible is strongly preheated at 500 to 550° C. for 1 hour, and after standing to cool, the mass is precisely measured. After taking 2 to 4 g of sample and placing it in the crucible, the mass is precisely measured, removing or displacing the cover of the crucible if necessary, and gentle heating is performed first, followed by gradual increase in the temperature to strong heating at 500 to 550° C. for 4 hours or longer, ashing it until no more carbides remain. After being allowed to cool, the mass is precisely measured. The residue is again ashed until reaching a constant mass, and after cooling, the mass is precisely measured and recorded as the ash content (%).

The sanitary article standard, incidentally, is an ash content of no greater than 0.65%.

The water absorption factor is the mass of water absorbed by the pulp fiber per unit mass. The water absorption factor is measured in the following manner.

(1) A bag (200 mm×200 mm) of a nylon net (250 mesh nylon net by NBC Meshtec, Inc.) is prepared, and its mass $N_0$ (g) is measured.

(2) Approximately 5 g of measuring sample is placed in the nylon net, and the mass $A_0$ (g) including that of the nylon net is measured.

(3) After placing 1 L of 0.9% physiological saline in a beaker, the prepared sample-containing nylon net bag is immersed therein and allowed to stand for 3 minutes.

(4) The bag is raised out and allowed to stand for 3 minutes on a draining net for drainage.

(5) The mass A (g) after drainage of the nylon net bag containing the sample is measured.

(6) Another set of nylon nets cut out to the same size is prepared, (3) and (4) are carried out in the same manner but without placement of the sample, and the mass N (g) of each of the nylon net bags alone after drainage is measured.

(7) The water absorption factor (times) is calculated by the following formula.

Water absorption factor=$(A-N-(A_0-N_0))/(A_0-N_0)$ (8) The measurement is conducted 10 times, and the average value of the 10 measurements is recorded.

EXAMPLES

Example 1

Evaluation of Decomposition and Removal of Polymer Absorbent by Ozone-Containing Gas Treatment After placing 1.5 g of polymer absorbent (super-absorbent polymer AQUA KEEP® SA60S by Sumitomo Seika Chemicals Co., Ltd.) in a 10 cm×20 cm mesh bag (25 cm-square, N-No. 250HD by NBC Meshtec, Inc.), it was immersed for 15 minutes in 400 mL of distilled water or 80 mL of physiological saline and allowed to absorb the water, after which it was transferred to a 2 L-volume ozone gas exposure tank, and treatment was conducted in the ozone gas exposure tank by circulating through ozone-containing gas adjusted to an ozone concentration of 50 g/m$^3$ (with dry air as the non-ozone gas) and an airflow rate of 1 mL/min for a prescribed time period, from an ozone generator (ED-OWX-2 ozone gas exposure tester by EcoDesign, Inc.). The dry mass of the polymer absorbent before and after the ozone-containing gas treatment (the mass after 24 hours of drying with a hot air drier at 105° C.) was measured, and the weight reduction percentage of the polymer absorbent was calculated by the following formula.

Polymer absorbent weight reduction percentage (%)=$(M_0-M_1)/M_0\times100$ where:
$M_0$: Dry mass of polymer absorbent before ozone-containing gas treatment
$M_1$: Dry mass of polymer absorbent after ozone-containing gas treatment The results are shown in Table 1.

TABLE 1

|  | Treatment time (h) | Ozone concentration (g/m$^3$) | Polymer absorbent mass reduction (%) |
|---|---|---|---|
| Distilled water | 1 | 50 | 94.5 |
|  | 2 | 50 | 100 |
| Physiological saline | 1 | 50 | 43.8 |
|  | 2 | 50 | 82.9 |

Example 2

Evaluation of Decomposition and Removal of Polymer Absorbent by High-Concentration Ozone-Containing Gas Treatment After placing 1.5 g of polymer absorbent (super-absorbent polymer AQUA KEEP® SA60S by Sumitomo Seika Chemicals Co., Ltd.) in a 10 cm×20 cm mesh bag (25 cm-square, N-No. 250HD by NBC Meshtec, Inc.), it was immersed for 15 minutes in 400 mL of distilled water or 80 mL of physiological saline and allowed to absorb the water, after which it was transferred to a 30 L-volume ozone gas exposure tank, and treatment was conducted in the ozone gas exposure tank by circulating through ozone-containing gas adjusted to an ozone concentration of 80 g/m$^3$ (with dry air as the non-ozone gas) and an airflow rate of 0.24 Nm$^3$/h for a prescribed time period, from an ozone generator (OS-25V ozone generator by Mitsubishi Electric Corp.). The dry mass of the polymer absorbent before and after the ozone-containing gas treatment (the mass after 24 hours of drying with a hot air drier at 105° C.) was measured, and the weight reduction percentage of the polymer absorbent was calculated by the formula shown above. The results are shown in Table 2.

TABLE 2

| | Treatment time (min) | Ozone concentration (g/m$^3$) | Polymer absorbent mass reduction (%) |
|---|---|---|---|
| Distilled water | 10 | 80 | 96.0 |
| | 20 | 80 | 100 |
| Physiological saline | 10 | 80 | 84.0 |
| | 20 | 80 | 100 |

Example 3

Treatment of Diaper by High-concentration Ozone-Containing Gas

After absorbing 200 mL of physiological saline with a commercially available paper diaper (Moony® M Size, by Unicharm Corp.), it was cut out to an approximately 5 cm square with scissors and the total amount was placed in a mesh bag (25 cm square, N-No. 250HD by NBC Meshtec, Inc.), and pre-treated in a 30 L-volume ozone gas exposure tank by 30 minutes of circulation of ozone-containing gas adjusted to an ozone concentration of 80 g/m$^3$ (with dry air as the non-ozone gas) and an airflow rate of 0.24 Nm$^3$/h for a prescribed time period, from an ozone generator (OS-25V ozone generator by Mitsubishi Electric Corp.). Eight such pre-treated diapers were loaded into a dual-tank miniature washing machine ("Seisei" AST-01 by Alumis Co.), and 6.5 L of tap water was added. After 15 minutes of washing, the liquid in the washing tub was drained and 6.5 L of tap water was freshly loaded. After another 15 minutes of washing, only the pulp fiber floating in the liquid inside the washing machine was skimmed off and placed in a mesh bag (25 cm square, N-No. 250HD by NBC Meshtec, Inc.), and dehydrated for 5 minutes in a dehydrating tank. The recovered pulp was rinsed with tap water for 15 minutes while in the mesh bag, and again dehydrated for 5 minutes in a dehydrating tank. The recovered pulp fiber was then dried for 24 hours in a hot air drier at 105° C. The ash content, water absorption factor and water retention factor of the obtained pulp fiber were evaluated. The evaluation results are shown in Table 3.

Comparative Example 1

After absorbing 200 mL of physiological saline with a commercially available paper diaper ("Moony" M size, by Unicharm Corp.), 8 such paper diapers were loaded into a dual-tank miniature washing machine ("Seisei" AST-01 by Alumis Co.), 80 g of CaO (product of Wako Pure Chemical Industries, Ltd.) was further loaded in, and then 6.5 L of a sodium hypochlorite aqueous solution at a 250 ppm concentration (sodium hypochlorite diluted with tap water, product of Wako Pure Chemical Industries, Ltd.) was added. After 15 minutes of washing, the liquid in the washing tub was drained, and 6.5 L of a sodium hypochlorite aqueous solution at a concentration of 250 ppm (sodium hypochlorite diluted with tap water, product of Wako Pure Chemical Industries, Ltd.) was freshly loaded in. After another 15 minutes of washing, only the pulp fiber floating in the liquid inside the washing machine was skimmed off and placed in a mesh bag (25 cm square, N-No. 250HD by NBC Meshtec, Inc.), and dehydrated for 5 minutes in a dehydrating tank. The recovered pulp fiber was rinsed with tap water for 15 minutes while in the mesh bag, and again dehydrated for 5 minutes in a dehydrating tank. The recovered pulp fiber was then dried for 24 hours in a hot air drier at 105° C. The ash content, water absorption factor and water retention factor of the obtained pulp fiber were evaluated. The evaluation results are shown in Table 3.

TABLE 3

| | Ash content (%) | Water absorption factor (g/g) | Water retention factor (g/g) |
|---|---|---|---|
| Pulp before treatment | 0.18 | 16.4 | 7.60 |
| Example 3 | 0.07 | 17.1 | 7.74 |
| Comp. Example 1 | 8.51 | 8.03 | 2.84 |

In Example 3 the performance exhibited was roughly equivalent to that of the pulp before treatment, but in Comparative Example 1, the absorption performance was significantly reduced due to the ash content.

The method for measuring the water retention factor is as follows.

[Method of Measuring Water Retention Factor]

The absorption factor-measured sample is placed in a centrifugal separator (Model H130 Centrifuge by Kokusan Centrifugation Co., Ltd., rotational speed: 850 rpm=150G) and dewatered at 150G for 90 seconds, and then the mass B (g) is measured.

$$\text{Water retention factor}=(B-N-(A_0-N_0))/(A_0-N_0)$$

The measurement is conducted 10 times, and the average value of the 10 measurements is recorded.

[Verification of Bleaching Effect]

A standard soiled fabric (EMPA111 blood-stained fabric by EMPA) used as the sample was treated for 20 minutes with ozone-containing gas at an ozone concentration of 80 g/m$^3$. When the color of the treated sample was visually observed, the color was found to have lightened from brown before treatment to light brown after treatment. It was thus confirmed that treatment of a polymer absorbent under ozone gas treatment conditions that allow decomposition and removal is able to decompose and remove blood stains, and also has a bleaching effect.

INDUSTRIAL APPLICABILITY

The method of the invention allows recovered pulp fiber to be satisfactorily utilized for regenerated production of sanitary products.

The invention claimed is:

1. A method for recovering pulp fiber from a used sanitary product including pulp fiber and a polymer absorbent, comprising the step of:
   treating the used sanitary product with an ozone-containing gas to decompose and remove at least a portion of the polymer absorbent in the used sanitary product which decomposed and removed portion of the polymer absorbent is gasified and removed as carbon dioxide, wherein a product of the ozone concentration of the ozone-containing gas and the treatment time with the ozone-containing gas is 500 to 12,000 $m^{-3} \cdot g \cdot min$.

2. The method according to claim 1, wherein the ozone concentration of the ozone-containing gas is 50 to 200 $g/m^3$.

3. The method according to claim 2, wherein the treatment time with the ozone-containing gas is 10 to 60 minutes.

4. The method according to claim 3, wherein the used sanitary product is treated with the ozone-containing gas to decompose and remove at least 90% of the polymer absorbent in the used sanitary product.

5. The method according to claim 2, wherein the used sanitary product is treated with the ozone-containing gas to decompose and remove at least 90% of the polymer absorbent in the used sanitary product.

6. The method according to claim 1, wherein the treatment time with the ozone-containing gas is 10 to 60 minutes.

7. The method according to claim 6, wherein the used sanitary product is treated with the ozone-containing gas to decompose and remove at least 90% of the polymer absorbent in the used sanitary product.

8. The method according to claim 1, wherein the used sanitary product is treated with the ozone-containing gas to decompose and remove at least 90% of the polymer absorbent in the used sanitary product.

9. The method according to claim 1, further comprising the steps of:
   stirring the used sanitary product that has been treated with the ozone-containing gas, in an aqueous solution or in water to decompose the used sanitary product into its constituent elements, and
   separating the pulp fiber from the decomposition product obtained by the decomposing step.

10. The method according to claim 1, comprising a step of separating apart at least a portion of the elements composing the used sanitary product and/or breaking up a portion of the used sanitary product before the step of treating the used sanitary product with an ozone-containing gas to decompose and remove at least a portion of the polymer absorbent in the used sanitary product.

11. The method according to claim 1, further comprising a step of drying the pulp fiber, the step of drying the pulp fiber resulting in dried pulp fiber having a moisture content of 5 to 13%.

12. The method according to claim 11, wherein the pulp fiber is dried at a temperature of 100 to 200° C.

13. The method according to claim 1, wherein after decomposition a polymer absorbent mass of the decomposed used sanitary product is reduced by 43.8% to 100%.

14. The method according to claim 1, further comprising a step of discharging the carbon dioxide together with the ozone-containing gas.

\* \* \* \* \*